United States Patent [19]

Bennett

[11] Patent Number: Plant 5,470

[45] Date of Patent: May 21, 1985

[54] MINIATURE ROSE PLANT

[76] Inventor: Cecelia L. D. Bennett, 489 Minot Ave., Chula Vista, Calif. 92010

[21] Appl. No.: 519,962

[22] Filed: Aug. 3, 1983

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant characterized by it's soft shell pink petals and vigorous growth habit.

1 Drawing Figure

The present invention relates to a new and distinct variety of a hardy, dwarf, miniature bush plant of the miniature class; the variety being primarily characterized as a light pink.

The variety is further characterized by:

Long stemmed exhibition-quality blooms, usually borne singly but may occasional be borne in sprays, held very erect and well above the foliage.

Has a slight fragrance.

The plant ranges in height from 12 to 36 inches. The branches are sturdy and erect, heavily branched with medium foliage covering. The plant is a moderate to heavy bloomer that does well in either the green house or outdoors.

The plant is very vigorous with good growing habits, well shaped and attractive in appearance, bearing numerous leaflets of average size.

The discriptive matter which follows pertains to roses grown and color values observed in plants and newly opened blooms in the month of June. The plants were grown outdoors in Chula Vista, Calif., and are believed to be accurate standards for this same cultivar in similar conditions of soil and climate elsewhere.

The seed parent was "Futura" (U.S. Plant Pat. No. 3,569), and the pollen parent was "Avandel" (U.S. Plant Pat. No. 4,366).

Subsequent to the origination of the variety, I have successfully reproduced it at TINY PETAL'S NURSERY located at aforesaid retaining the distinguishing characteristics through succeeding propagations by cuttings.

The color photograph illustrates the variety.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf, bushy, green house or outdoor, garden decoration and exhibition-quality potted plant.

Class: Miniature.

Variety name: Pink Porcelain.

Flowers borne: One to a stem or in occasional sprays of 3 to 5 or more on erect stems with foliage well below the blooms.

Quantity of bloom: Moderate to heavy both outdoors and green house grown.

Bud:

*Peduncle.*—Medium to long (averaging 30 to 50 mm); average diameter and sturdy; medium green with occasional tinting of bronze.

*Hairs.*—Extremely small and delicate; very numerous; bronze in color; located over the entire surface of the peduncle, calyx and the outer surface of the sepals.

*Calyx.*—Color is Pod Green (061/1 page 120) from base of the calyx tube to the ends of the sepals with slight tinting of bronze created by the presence of bronze-colored hairs over the surface.

*Opening.*—Opens well in all weather.

Bloom:

*Size when fully open.*—Average to large for a miniature variety 50 to 60 mm (2 to 2½ inches).

*Petalage.*—Double; averaging about 20 petals, arranged regularly plus petaloids (8 to 12 or more).

*Form.*—Urn-shaped to ovoid as the bloom progresses. The petals remain at first somewhat tightly cupped with the tips and/or margins reflexed outward, becoming later at maturity more loosely cupped, with the tips and/or margins reflexed outward; and the outermost petals reflexing more tightly as the bloom matures with the margins rolling under, forming a peak at the apex of the petals.

Petals: Fairly thick with good substance; matte finish.

*Shape.*—Outer petals are of a broad obovate form with a slight peak at the apex. The intermediate petals are very much like the outer petals only narrower. The inner petals are more like broad lanceolates, and the petaloids are small and irregularly shaped.

Color: Newly opened flowers from plants grown outdoors (June 1983), Chula Vista, Calif.:

*Outside petals.*—Upper Surface — Egyptian Buff (407/3 page 122) with a small area at the base of Empire Yellow (603/1 page 66). Under Surface — The same as upper surface.

*Intermediate petals.*—Upper Surface — Egyptian Buff (407/3 page 122) gradually deepening to Shell Pink (516/3 page 135) near the base, with a very small area at the base of Empire Yellow (603/1 page 66). Under Surface — The same as upper surface.

*Inner petals.*—Upper Surface — Shell Pink (516/2 page 135) with a small area at the base of Empire Yellow (603/1 page 66). Under Surface — The same as upper surface.

*General color effect.*—Newly opened flowers — Soft shell pink with lighter tones on the outer petals. Three days open — slightly paler than newly opened. Spent petals drop off cleanly, except petaloids.

*Flower longevity.*—(June 1983) Plant in pot 6 to 8 days from bud with sepals down to fully open bloom. Holding at fully open with only slight fading of color for additional 3 to 4 days before outer petals roll under forming peaking at the apex of outer petals only. Holding at final stage for additional 3 to 4 days before dropping petals. Cut blooms at livingroom temperature 4 to 5 days or longer.

Reproductive organs:

*Stamens.*—A generous amount arranged uniformly around the pistil.

*Filament.*—Varying in lengths.

*Pollen.*—Abundant.

*Pistil.*—Average length, abundant and spreading.

*Styles.*—Average to long; pale yellow at the bottom, becoming red near the top.

*Ovaries.*—All encased in calyx.

*Hips.*—Some.

*Seed.*—Few or none.

*Sepals.*—Permanent; lanceolate-shaped with some foliation of the margins: recurves against the peduncle as the bloom matures.

Foliage:

*Leaves.*—Five to seven, average in size.

*Leaflets.*—Broad ovate-shaped.

*Margin.*—Very serrated with occasional reddish tinge on the edge, especially noticeable on the newer foliage.

*Color.*—Ranging from Fern Green (086/2 page 186) with a tinge of bronze in the newer leaves to Spinach Green (0960/2 page 187) in the mature leaves. The upper surfaces are satiny and the under surfaces have a matte finish of a slightly lighter color than the upper surface.

*Rachis.*—Medium strength; upper side may have a few small hairs; grooved; under side smooth except for a few sparse thorns.

*Stipules.*—Varying in length from medium to long; average width; tapering auricles angled outward at about 45 degrees.

Growth:

*Habit.*—Dwarf; bushy; much branched; average to large size for a miniature rose plant.

*Growth.*—Vigorous.

*Canes.*—Medium; sturdy; held very erect.

*Main stems.*—Color — Spinach Green (0960/2 page 187) to Spinach Green (0960/3 page 187) with some tinting of bronze, especially noticeable on the newer stems.

*Thorns.*—Average; slender; hooked slightly downward; color — red to brown. Prickles — none. Hairs — Present on upper surface of rachis and in abundance on the peduncle and sepals.

*Branches.*—Color — Spinach Green (0960/2 page 187) to Spinach Green (0960/3 page 187) with some tinting of bronze. Medium length; slender; sturdy; very erect. Thorns — Usually 1 to 3 located below each leaflet or midway between the leaflets; hooked slightly downward. Prickles — None. Hairs — None.

The miniature rose plant and its flowers as herein described may vary in slight detail due to climatic, soil, and cultural conditions under which the variety may be grown; the present description being of the variety as grown at Chula Vista, Calif.

The following is claimed:

1. A new and distinct variety of miniature rose plant of hardy, dwarf, bushy, much branched habit, substantially as illustrated and described, characterized by its soft shell pink blooms and vigorous growth habit, easy to propagate from cuttings, with flowers borne both singly and in sprays of 3 to 5 or more.

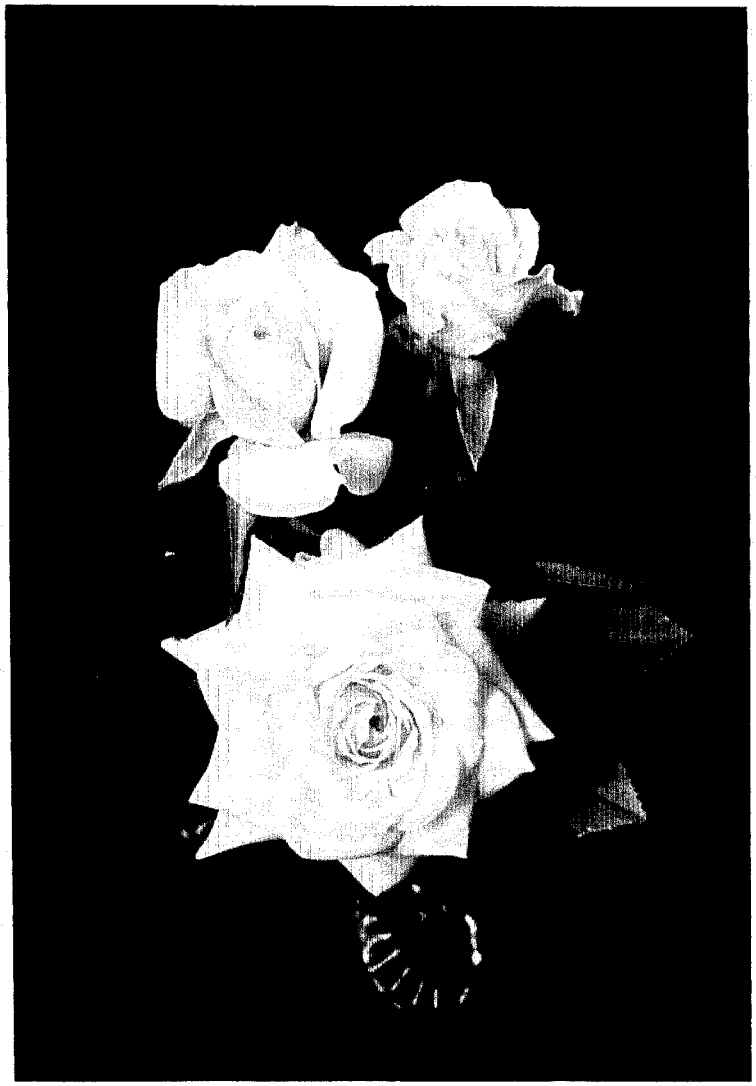

* * * * *